(12) United States Patent
Gross

(10) Patent No.: US 8,747,818 B1
(45) Date of Patent: Jun. 10, 2014

(54) SELF-TANNING COMPOSITIONS

(76) Inventor: Dennis Gross, New York, NY (US)

( * ) Notice: Subject to any disclaimer, the term of this patent is extended or adjusted under 35 U.S.C. 154(b) by 50 days.

(21) Appl. No.: 13/367,474

(22) Filed: Feb. 7, 2012

Related U.S. Application Data

(60) Provisional application No. 61/440,066, filed on Feb. 7, 2011.

(51) Int. Cl.
*A61K 8/00* (2006.01)
*A61K 36/76* (2006.01)
*A61K 36/00* (2006.01)

(52) U.S. Cl.
USPC .............................. 424/59; 424/401

(58) Field of Classification Search
USPC .................................. 424/59, 401
See application file for complete search history.

(56) References Cited

U.S. PATENT DOCUMENTS

| 6,451,293 | B1 * | 9/2002 | Schreier et al. ............ 424/59 |
| 7,378,084 | B2 * | 5/2008 | Dueva-Koganov et al. .... 424/59 |
| 2001/0002396 | A1 * | 5/2001 | Achkar .................... 514/167 |
| 2007/0048233 | A1 * | 3/2007 | Bommarito ................ 424/59 |
| 2010/0034760 | A1 * | 2/2010 | Rudolph et al. ............ 424/59 |

FOREIGN PATENT DOCUMENTS

JP 02178218 A * 7/1990

* cited by examiner

*Primary Examiner* — Gina C Justice
(74) *Attorney, Agent, or Firm* — Kenyon & Kenyon LLP

(57) ABSTRACT

This invention is related to a sunless tanning composition comprising at least one self-tanner and at least one vitamin D compound, wherein the at least one self-tanner is selected from dihydroxyacetone, erythrulose, or a mixture thereof.

22 Claims, No Drawings

SELF-TANNING COMPOSITIONS

CROSS-REFERENCE TO RELATED APPLICATION

This patent application claims the benefit of U.S. Provisional Application No. 61/440,066, filed on Feb. 7, 2011, the disclosure of which is herein incorporated by reference in its entirety.

The invention is related to improved self-tanning compositions that can achieve pleasing, naturally looking sun tan without potentially harmful exposures to sunlight.

BACKGROUND OF INVENTION

Sun tan is the browning of the skin as a result of sunlight exposures. Other than sun tan, sunlight can damage the skin with the potential of causing wrinkles, age spots, and even cancers of the skin. The browning of the skin is actually the result of our bodies' protective mechanism against sunlight. Exposures to sunlight could lead to DNA damage in the skin cells. In addition, exposures of the skin to the ultraviolet portion, UVA in particular, of sunlight can cause the oxidation of the melanin pigment in the skin resulting in the deepening in color of melanin in a short time and increased synthesis of melanin in skin cells after two or three days. The oxidized melanin and the increased amount of melanin in the skin cells offer protection against future exposures to sunlight by shielding the skin cell DNA from the harmful ultraviolet radiation of sunlight. The oxidized melanin and increased amount of melanin cause sun tan.

Sun tan has long been regarded as a side effect of outdoor exposures to sunlight for some people working outdoor or for travelers in some regions of the world. Appropriate clothing and hats have been worn to reduce sunlight exposures reducing the chance of sunburn, and secondarily the chance or degree of sun tanning. However, with recent lifestyle changes and changes in beauty standards, sun tan has more and more been accepted by some segments of the population as desirable nowadays. Some people even actively seek sun tan for what they perceive to be its aesthetic value. These people would deliberately increase sunlight exposures, for example by sun bathing, in order to achieve sun tanning. Because sun bathing can cause sunburn, some people may apply sunscreen that would reduce exposures to the damaging portion of the ultraviolet radiation of sunlight in order to prolong sun bathing with reduced sunburn risk.

Others may want to get sun tan with artificial means including exposures to ultraviolet radiation under UV lamps in sun tanning booths, application of skin lotions or creams containing bronzers, certain brown dyes, to stain the skin temporarily, or application of self-tanning compositions to the skin. The self-tanning compositions contain a self-tanner such as dihydroxyacetone (DHA) or erythrulose. The self-tanner chemical reacts with proteins in the dead cells of the stratum corneum to produce a brown substance. Because the dead cells are desquamated in two to three weeks, the tanning does not last long. Despite the long availability of sunless tanning products, there is a need for improved sunless tanning compositions that can produce better tanning effects. The present invention is aimed at improving sunless tanning compositions.

SUMMARY OF THE INVENTION

The present invention provides an improved sunless tanning composition comprising at least one self-tanner and at least one vitamin D compound with optional inclusion of at least one physiologically acceptable carrier, at least one physiologically acceptable excipient, at least one physiologically acceptable aesthetic component, at least one skin conditioning agent and/or at least one skin care agent, wherein the at least one self-tanner is selected from dihydroxyacetone and erythrulose. Preferably, the at least one self-tanner is dihydroxyacetone, but a mixture of dihydroxyacetone and erythrulose can be used.

The present invention, in addition, provides a towelette comprising a towel, e.g., a sheet or pad, containing an improved sunless tanning composition and enclosed in a leakproof container, e.g., a wrap, foil or shield, wherein the towel, e.g., the sheet or pad, comprises a fibrous or non-fibrous absorbent material that is woven or nonwoven, and wherein the improved sunless tanning composition comprises at least one self-tanner and at least one vitamin D compound with optional inclusion of at least one physiologically acceptable carrier, at least one physiologically acceptable excipient, at least one physiologically acceptable aesthetic component, at least one skin conditioning agent and/or at least one skin care agent, wherein the at least one self-tanner is selected from dihydroxyacetone and erythrulose.

The present invention also is directed to a process for making the improved sunless tanning composition of the invention, comprising mixing at least one self-tanner and at least one vitamin D compound with optional inclusion of at least one physiologically acceptable carrier, at least one physiologically acceptable excipient, at least one physiologically acceptable aesthetic component, at least one skin conditioning agent and/or at least one skin care agent, wherein the at least one self-tanner is selected from dihydroxyacetone and erythrulose. Preferably, the at least one self-tanner is dihydroxyacetone, but a mixture of dihydroxyacetone and erythrulose can be used.

The present invention also provides a method of obtaining a sun tan, comprising the step of applying a sunless tanning composition to the skin, said sunless tanning composition comprising at least one self-tanner and at least one vitamin D compound with optional inclusion of at least one physiologically acceptable carrier, at least one physiologically acceptable excipient, at least one physiologically acceptable aesthetic component, at least one skin conditioning agent and/or at least one skin care agent, wherein the at least one self-tanner is selected from dihydroxyacetone and erythrulose. Preferably, the at least one self-tanner is dihydroxyacetone, but a mixture of dihydroxyacetone and erythrulose can be used. The method can be conducted without any sunlight exposures and/or ultraviolet radiation exposures. The method, however, does not require the absence of sunlight exposures and/or ultraviolet radiation exposures. The sunless tanning composition of the invention can be applied to the skin of the body, head, face, neck, ears, torso, limbs, arms, forearms, hands, legs, and/or feet, The present invention, in addition, provides a process of preparing a towelette comprising a towel, e.g., a sheet or pad, containing an improved sunless tanning composition and enclosed in a leakproof container, e.g., a wrap, foil or shield, said process comprising impregnating the towel, e.g., the sheet or pad, with the improved sunless tanning composition, and then enclosing the resulting pad or sheet in the leakproof container, e.g., the wrap, foil or shield, wherein the towel, e.g. the sheet or pad, comprises a fibrous or non-fibrous absorbent material that is woven or nonwoven, and wherein the improved sunless tanning composition comprises at least one self-tanner and at least one vitamin D compound with optional inclusion of at least one physiologically acceptable carrier, at least one physiologically acceptable excipient, at least one physiologically acceptable aesthetic component, at least one skin conditioning agent and/or at least one skin care agent, wherein the at least one self-tanner is selected from dihydroxyacetone and erythrulose.

DETAILED DESCRIPTION OF THE INVENTION

The term "dihydroxyacetone" or "DHA" refers to a compound having a chemical formula of $HOCH_2C(O)CH_2OH$. Dihydroxyacetone (DHA) is also named as 1,3-dihydroxyacetone or 1,3-dihydroxypropan-2-one, having the chemical structure of formula (I).

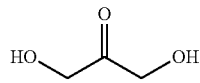
(I)

As used herein, the term "erythrulose" refers to a ketose with a chemical formula of $HOCH_2C(O)CH(OH)CH_2OH$. The term "erythrulose" includes a compound named 1,3,4-trihydroxybutan-2-one, having the chemical structure of formula (II).

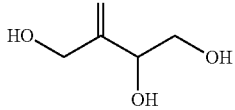
(II)

A preferred form of "erythrulose" is D-erythrulose or (R)-1,3,4-trihydroxybutan-2-one, having the chemical structure of formula (III).

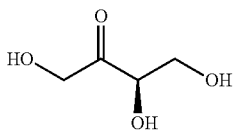
(III)

As used herein, the term "vitamin D compound" refers to pro-vitamin D, calciferol, vitamin $D_1$ (a molecular complex of vitamin $D_2$ and lumisterol), vitamin $D_2$ (ergocalciferol), vitamin $D_3$ (cholecalciferol), vitamin $D_4$ (22-dihydroergocalciferol) and/or vitamin $D_5$ (sitocalciferol). The term "pro-vitamin D" refers to compounds that can be converted to vitamin D2 or vitamin D3 in the skin, wherein the pro-vitamin D is selected from ergosterol, preergocalciferol, 7-dehydrocholesterol and precholecalciferol. Preferred forms of "vitamin D compound" are vitamin $D_2$ and vitamin $D_3$. The chemical structures of vitamin $D_2$ and vitamin $D_3$ are shown in formula (IV) and formula (V), respectively.

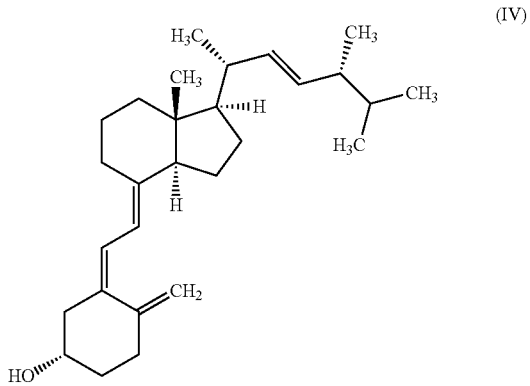 [SMILES: C=C1CC[C@H](O)C/C1=C/C=C1\CCC[C@]2(C)[C@@H]([C@H](C)/C=C/[C@H](C)C(C)C)CC[C@@H]12]

The term "physiologically acceptable" modifying a substance means that the substance is considered to be safe when administered to an individual. Preferably, a "physiologically acceptable" substance would cause little or no allergic response.

The term "physiologically acceptable carrier" refers to a carrier, such as water and ethylene glycol, that is regarded to be safe when used to carry the self-tanner and vitamin D of the self-tanning composition of the invention. In some of the embodiments of the invention, the at least one physiologically acceptable carrier is a liquid, e.g., water or a cosmetically acceptable aqueous buffer having a pH of about 7.0 to about 7.4, and, more preferably, the water or aqueous buffer is purified and/or sterile.

The term "physiologically acceptable excipient" refers to an excipient, such as an emollient, that is regarded to be safe when used to perform an accessory function for the self-tanning composition of the invention. In some of the embodiments of the invention, the at least one physiologically acceptable excipient is selected from emollients/humectants/moisturizers, surfactant/emulsifying agents, absorbents, anti-foaming agents, binders, biological additives, chelating agents, denaturants, preservatives, solubilizing agents, solvents and thickening agents.

As used herein, the term "towelette" refers to a packet containing a towel enclosed in a container that prevents the leakage or evaporation of any liquid applied to the towel, wherein the towel has a liquid applied to it. The container of the towelette is impermeable to moisture or vapors. Preferably, the container of the towelette is a leakproof pouch, wrap, foil or shield, made of material(s) such as aluminum, polymeric material(s) or combination of layers thereof. The towel is made of a woven or non-woven fibrous or non-fibrous material that can absorb a liquid. The towel is preferably in the form of a sheet or pad. Preferably, the towel is made of a fibrous material, wherein the fibrous material can be woven or, more preferably, non-woven. The towel can be made of a cellulosic material, paper, wood-pulp-containing material such as rayon or viscose, or cotton-containing material, or a mixture thereof.

Suitable emollients/humectants/moisturizers that can be used in the self-tanning composition of the invention include the emollients and moisturizing agents disclosed below. Examples of emollients that can be used are phospholipids, ceramide, glycerin, cetyl alcohol, cetearyl isononanoate, cetearyl octanoate, decyl oleate, isooctyl stearate, coco caprylate/caprate, ethylhexyl hydroxystearate, ethylhexyl isononanoate, isoproyl palmitate, isopropyl isostearate, isopropyl myristate, oleyl oleate, hexyl laurate, paraffinum liquidum, PEG-75 lanolin, PEG-7 glyceryl cocoate, petrolatum, ozokerite, cyclomethicone, dimethicone, dimethicone copolyol, dicaprylyl ether, butyrospermum parkii, buxus chinensis, canola, carnauba cera, copernicia cerifera, *oenothera biennis*, elaeis guineensis, prunus dulcis, squalane, *zea mays*, glycine soja, *helianthus annuus*, lanolin, hydrogenated castor oil, hydrogenated coconut oil, avocado oil, hydrogenated polyisobutene, sucrose cocoate, stearoxy dimethicone, lanolin alcohol, isohexadecane. Examples of moisturizing agents that can be used are butylene glycol, cetyl alcohol, dimethicone, dimyristyl tartrate, glucose, glycereth-26, glycerin, glyceryl stearate, hydrolyzed milk protein, lactic acid, lactose and other sugars, laureth-8, lecithin, octoxyglycerin, PEG-12, PEG-135, PEG-150, PEG-20, PEG-8, pentylene glycol, hexylene glycol, phytantriol, polyquaternium-39, PPG-20 methyl glucose ether, propylene glycol, sodium hyaluronate, sodium lactate, sodium PCA (sodium salt of 1-pyrrolidone carboxylic acid), sorbitol, succinoglycan, synthetic beeswax, tri-C14 15 alkyl citrate and starch.

Suitable surfactant/emulsifying agents include cetereths, ceteths, laneths, laureths, isosareths, steareths, cetyl alcohol, deceths, dodoxynols, glyceryl palmitate, glyceryl stearate, laneths, myreths, nonoxynols, octoxynols, oleths, PEG-castor oil, poloxamers (e.g., poloxamer 407), poloxamines, polysorbates, sodium laurate, ammonium laureth sulfate, sodium laureth sulfate, sodium lauroyl sarcosinate, sodium lauroyl taurate, sodium lauryl sulfate, sodium methyl cocoyl taurate, sodium methyl oleoyl taurate, sodium nonoxynol sulfate, sodium cetyl sulfate, sodium cetearyl sulfate, sodium cocoate, sodium cocoyl isethionate and sodium cocoyl sarcosinate. Preferred surfactants include octoxynol-9 and polysorbate-20.

Examples of suitable absorbents are alumina, aluminum hydroxide, aluminum magnesium silicate, aluminum silicate, aluminum starch octenylsuccinate, bentonite, bismuth oxychloride, boron nitride, calcium carbonate, clay, cornstarch, fuller's earth, kaolin, magnesium, magnesium carbonate, magnesium hydroxide, montmorillonite, rice starch, silica, silicate, silt, sodium carbonate, talc and zeolite.

Examples of chelating agents are ethylene diaminetetraacetic acid (EDTA), sodium or potassium salts of EDTA such as EDTA disodium salt, EDTA trisodium salt and EDTA tetrasodium salt, cyclodextrin, pentasodium pentetate, phytic acid, potassium citrate and potassium gluconate. In some of the embodiments of the invention, the chelating agents are selected from EDTA, EDTA disodium salt, EDTA trisodium salt, EDTA tetrasodium salt and phytic acid.

Examples of suitable preservatives include imidazolidinyl urea, diazolidinyl urea, phenoxyethanol, methylparaben, ethylparaben and propylparaben.

Examples of thickening agents include isopropyl myristate, isopropyl palmitate, isodecyl neopentanoate, squalene, mineral oil, $C_{12}$-$C_{15}$ benzoate and hydrogenated polyisobutene.

The at least one aesthetic component can be at least one of fragrances, pigments, colorants, essential oils, skin sensates and astringents. Examples of the suitable essential oils are olive oil, rose oil, palm oil, lavender oil, almond oil, *Oenothera biennis* (evening primrose) oil, clove oil, eucalyptus oil, peppermint oil and spearmint oil. Suitable aesthetic components include clove oil, menthol, camphor, eucalyptus oil, eugenol, methyl lactate, bisabolol, witch hazel distillate (preferred) and green tea extract (preferred).

The term "skin care agent" refers to an agent that has one or more beneficial effects on the care and/or hygiene of the skin. The skin care agent can be selected from the group consisting of antioxidants, free-radical scavengers, antimicrobial agents, anti-acne agents, reducing agents, vitamins, skin protecting agents, skin bleaching agents, skin conditioning agents, skin soothing agents, skin healing agents, collagen promoters, exfoliators, chelators, hair removers, anti-erythema agents, anti-redness agents, anti-rosacea agents, depuffing agents, anti-edema agents, anti-swelling agents, hyaluronic acid, green tea extract, *Phyllanthus emblica* (Amla), arnica, chamomile extract, cucumber extract and exfoliants. In some of the embodiments of the invention, the skin care agent is selected from skin protecting agents, skin conditioning agents, antioxidants, anti-acne agents, collagen promoters, soluble collagen, and mixtures thereof. In further embodiments of the invention, the skin care agent is selected from antiwrinkle agents, anti-skin-atrophy agents, antioxidants and anti-acne agents.

The term "skin conditioning agent" refers to an agent that can maintain the skin in a good condition. The skin conditioning agents can be emollients, humectants and moisturizers, which include urea; guanidine; aloe vera; glycolic acid and glycolate salts such as ammonium and quaternary alkyl ammonium; lactic acid and lactate salts such as sodium lactate, ammonium lactate and quaternary alkyl ammonium lactate; polyhydroxy alcohols such as sorbitol, glycerol, hexanetriol, propylene glycol, butylene glycol, hexylene glycol, polyethylene glycol; carbohydrates such as alkoxylated glucose; starches; starch derivatives; glycerin; pyrrolidone carboxylic acid (PCA); lactamide monoethanolamine; acetamide monoethanolamine; volatile silicone oils; nonvolatile silicone oils; and mixtures thereof. Suitable silicone oils can be polydialkylsiloxanes, polydiarylsiloxanes, polyalkarylsiloxanes and cyclomethicones having 3 to 9 silicon atoms. Phospholipids, *Salix alba* (willow) bark extract, or a mixture thereof, can also be used as the skin conditioning agent. In some of the embodiments of the invention, the skin conditioning agent is selected from cyclomethicone, dimethiconol, phospholipids and *Salix alba* (willow) bark extract.

Skin soothing agents include bisabolol.

As used herein, the term "anti-acne agent" means a substance that have a beneficial effect in treating or preventing acne. Suitable anti-acne agents can be drying agents, keratolytic agents, epidermolytic agents, antimicrobial agents and retinoids. Examples of anti-acne agents include sulfur, resorcinol, glycolic acid, lactic acid, pyruvic acid, salicylic acid, retinoic acid, derivatives of retinoic acid, and antimicrobial agents, e.g., farnesol, benzoyl peroxide, erythromycin, triclosan, azelaic acid, clindamycin, chlorhexidine, neomycin, miconazole, clotrimazole and tetracycline. Suitable anti-acne agents include salicylic acid; 5-octanoyl salicylic acid; resorcinol; retinoids such as retinoic acid and its derivatives; sulfur-containing D and L amino acids other than cysteine; lipoic acid; antibiotics and antimicrobials such as benzoyl peroxide, octopirox, tetracycline, 2,4,4'-trichloro-2'-hydroxydiphenyl ether, 3,4,4'-trichlorobanilide, azelaic acid, phenoxyethanol, phenoxypropanol, phenoxisopropanol, ethyl acetate, clindamycin and melclocycline; flavonoids; and bile salts such as scymnol sulfate, deoxycholate and cholate.

The skin protecting agents are agents that protect the skin against chemical irritants and/or physical irritants, e.g., UV light, including sunscreens, anti-acne additives, anti-wrinkle and anti-skin atrophy agents.

Suitable UV blocking agents include 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomethyl salicylate, octyl salicylate, 4,4'-methoxy-t-butyldibenzoylmethane, 4-isopropy dibenzoylmethane, 3-benzylidene camphor, 3-(4-methylbenzylidene) camphor, anthanilates, ultrafine titanium dioxide, zinc oxide, iron oxide, silica, 4-N,N-(2-ethylhexyl) methylaminobenzoic acid ester of 2,4-dihydroxybenzophenone, 4-N,N-(2-ethylhexyl)-methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone and 4-N,N(2-ethylhexyl)-methylaminobenzoic acid ester of 4-(2-hydroxyethoxy) dibenzoylmethane.

Examples of anti-wrinkle and anti-skin atrophy agents are retinoic acid and its derivatives, retinol, retinyl esters, salicylic acid and its derivatives, sulfur-containing D and L amino acids except cysteine, alpha-hydroxy acids (e.g., glycolic acid and lactic acid), phytic acid, lipoic acid and lysophosphatidic acid.

Suitable collagen promoters are peptides, soy proteins, soy extract, ascorbic acid, alpha-hydroxy acids, *Phyllanthus emblica* (Amla) and *Phyllanthus emblica* fruit extract.

Examples of antioxidants and/or free-radical scavengers include ascorbic acid, salts of ascorbic acid such as ascorbyl palmitate and sodium ascorbate, ascorbyl glucosamine, vitamin E (i.e., tocopherols such as α-tocopherol), derivatives of vitamin E (e.g., tocopheryl acetate), retinoids such as retinoic acid, retinol, trans-retinol, cis-retinol, mixtures of trans-retinol and cis-retinol, 3-dehydroretinol and derivatives of vitamin A (e.g., retinyl acetate, retinal and retinyl palmitate, also known as tetinyl palmitate), lipoic acid, sodium citrate, sodium sulfite, lycopene, anthocyanids, bioflavinoids (e.g., hesperitin, naringen, rutin and quercetin), superoxide dismutase, glutathione peroxidase, butylated hydroxytoluene (BHT), butylated hydroxyanisole (BHA), indole-3-carbinol, pycnogenol, melatonin, sulforaphane, pregnenolone, lipoic acid and 4-hydroxy-5-methyl-3[2H]-furanone.

The antimicrobial agents can be antibacterial agents and/or antifungal agents. Examples of the antimicrobial agents include farnesol, benzoyl peroxide, erythromycin, tetracycline, triclosan, azelaic acid, clindamycin, chlorhexidine, neomycin, miconazole and clotrimazole.

Suitable exfoliants include hydroxy carboxylic acids such as alpha hydroxy acids or beta hydroxy acids, keto acids and hydroxybenzoic acids. Examples of exfoliants that can be used are glycolic acid, lactic acid, malic acid, tartaric acid, citric acid, ascorbic acid, mandelic acid, azelaic acid, glyceric acid, tartronic acid, gluconic acid, benzylic acid, pyruvic acid, 2-hydroxybutyric acid and salicylic acid.

One of the embodiments of the self-tanning composition of the present invention comprises the following components: dihydroxyacetone, erythrulose, ergocalciferol, ethoxydiglycol, glycerin, glycolic acid, lactic acid, retinyl palmitate, panthenol, ascorbyl palmitate, tocopheryl acetate, *Salix alba* (willow) bark extract, hydrolyzed soy protein, phospholipids, *Phyllanthus emblica* fruit extract, phytic acid, disodium EDTA, phenoxyethanol and water.

Another embodiment of the self-tanning composition of the present invention comprises: 70.244 wt % water, 15.000 wt % ethoxydiglycol, 7.000 wt % dihydroxyacetone, 5.000 wt % glycerin, 1.000 wt % hydrolyzed soy protein, 1.000 wt % phenoxyethanol, 0.170 wt % glycolic acid, 0.210 wt % lactic acid, 0.100 wt % erythrulose, 0.100 wt % panthenol, 0.100 wt % *Phyllanthus emblica* fruit extract, 0.050 wt % disodium EDTA, 0.010 wt % phytic acid, 0.010 wt % *Salix alba* (willow) bark extract, 0.002 wt % phospholipids, 0.001 wt % ascorbyl palmitate, 0.001 wt % ergocalciferol, 0.001 wt % retinyl palmitate and 0.001 wt % tocopheryl acetate.

With the invention disclosed above, some of the embodiments of the invention are exemplified below. It is understood that the embodiments shown in the examples below can be broadened according to the generic or specific disclosures described above with optional supplementation using knowledge from the art.

Example 1

A self-tanning composition of the present invention was prepared by mixing the ingredients according to the following formula:
70.244 wt % water,
15.000 wt % ethoxydiglycol,
7.000 wt % dihydroxyacetone,
5.000 wt % glycerin,
1.000 wt % hydrolyzed soy protein,
1.000 wt % phenoxyethanol,
0.210 wt % lactic acid,
0.170 wt % glycolic acid,
0.100 wt % erythrulose,
0.100 wt % panthenol,
0.100 wt % *Phyllanthus emblica* fruit extract,
0.050 wt % disodium EDTA,
0.010 wt % phytic acid,
0.010 wt % *Salix alba* (willow) bark extract,
0.002 wt % phospholipids,
0.001 wt % ascorbyl palmitate,
0.001 wt % ergocalciferol,
0.001 wt % retinyl palmitate and
0.001 wt % tocopheryl acetate.

This self-tanning composition was applied to a pad made of nonwoven viscose fibers and polyethylene terephthalate (PET). To make a towelette of the invention, the pad containing the self-tanning composition was enclosed in a foil made of polyethylene terephthalate, linear low density polyethylene (linear "LDPE"), WLDPE, aluminum foil, and ethylene acrylic acid copolymer (EAA).

Example 2

Another embodiment of the self-tanning composition of the present invention comprises the following ingredients was prepared by mixing the ingredients:
68.474 wt % water,
15.000 wt % ethoxydiglycol,
7.000 wt % dihydroxyacetone,
5.600 wt % glycerin,
1.000 wt % hydrolyzed soy protein,
1.000 wt % phenoxyethanol,
0.600 wt % butylene glycol,
0.360 wt % *Larrea divaricata* extract,
0.210 wt % lactic acid,
0.200 wt % fragrance, 0.170 wt % glycolic acid,
0.100 wt % panthenol,
0.100 wt % *Phyllanthus emblica* fruit extract,
0.050 wt % disodium EDTA,
0.050 wt % erythrulose,
0.050 wt % lecithin,
0.010 wt % caffeine,
0.010 wt % phytic acid,
0.010 wt % *Salix alba* (willow) bark extract,
0.002 wt % phospholipids,
0.001 wt % ascorbyl palmitate,
0.001 wt % ergocalciferol,
0.001 wt % retinyl palmitate and
0.001 wt % tocopheryl acetate.

This self-tanning composition was applied to a pad made of nonwoven rayon fibers and polypropylene. The pad containing the self-tanning composition was enclosed in a foil made of polyethylene terephthalate, low density polyethylene (LDPE), linear LDPE, aluminum foil, and ethylene acrylic acid copoymer (EAA) to form a towelette.

The invention claimed is:

1. A sunless tanning composition comprising at least one self-tanner and at least one vitamin D compound, wherein the at least one self-tanner is a mixture of dihydroxyacetone and erythrulose, said composition further comprising ethoxydiglycol, glycerin, hydrolyzed soy protein, phenoxyethanol, glycolic acid, lactic acid, panthenol, *Phyllanthus emblica* fruit extract, disodium EDTA, phytic acid, *Salix alba* (willow) bark extract, phospholipids, ascorbyl palmitate, retinyl palmitate and tocopheryl acetate.

2. A sunless tanning composition comprising at least one self-tanner and at least one vitamin D compound, wherein the at least one self-tanner is selected from dihydroxyacetone, erythrulose, or a mixture thereof, said composition further comprising a substance selected from hydrolyzed soy protein, *Larrea divaricata* extract, *Salix alba* (willow) bark extract, and phospholipids.

3. A sunless tanning composition comprising at least one self-tanner and at least one vitamin D compound, wherein the at least one self-tanner is a mixture of dihydroxyacetone and erythrulose, said composition further comprising ethoxydiglycol, glycerin, hydrolyzed soy protein, phenoxyethanol, butylene glycol, *Larrea divaricata* extract, lactic acid, glycolic acid, panthenol, *Phyllanthus emblica* fruit extract, disodium EDTA, lecithin, caffeine, phytic acid, *Salix alba* (willow) bark extract, phospholipids, ascorbyl palmitate, retinyl palmitate and tocopheryl acetate.

4. The composition of claim 1 in a towelette, wherein the composition is in or on a towel of the towelette.

5. The composition of claim 2 in a towelette, wherein the composition is in or on a towel of the towelette.

6. The composition of claim 3 in a towelette, wherein the composition is in or on a towel of the towelette.

7. A method of obtaining suntan in a subject, comprising applying the composition of claim 1 to the skin of at least a portion of the body of the subject interested in obtaining the suntan.

8. A method of obtaining suntan in a subject, comprising applying the composition of claim 2 to the skin of at least a portion of the body of the subject interested in obtaining the suntan.

9. A method of obtaining suntan in a subject, comprising applying the composition of claim 3 to the skin of at least a portion of the body of the subject interested in obtaining the suntan.

10. The composition of claim 1, wherein the at least one vitamin D compound is selected from pro-vitamin D, calciferol, vitamin $D_1$, vitamin $D_2$, vitamin $D_3$, vitamin $D_4$ and/or vitamin $D_5$.

11. The composition of claim 2, wherein the at least one vitamin D compound is selected from pro-vitamin D, calciferol, vitamin $D_1$, vitamin $D_2$ (ergocalciferol), vitamin $D_3$ (cholecalciferol), vitamin $D_4$ (22-dihydroergocalciferol) and/or vitamin $D_5$ (sitocalciferol).

12. The composition of claim 3, wherein the at least one vitamin D compound is selected from pro-vitamin D, calciferol, vitamin $D_1$, vitamin $D_2$, vitamin $D_3$, vitamin $D_4$ and/or vitamin $D_5$.

13. The composition of claim 10, wherein the at least one vitamin D compound is selected from vitamin $D_2$, vitamin $D_3$ or a mixture thereof.

14. The composition of claim 11, wherein the at least one vitamin D compound is selected from vitamin $D_2$, vitamin $D_3$ or a mixture thereof.

15. The composition of claim 12, wherein the at least one vitamin D compound is selected from vitamin $D_2$, vitamin $D_3$ or a mixture thereof.

16. The composition of claim 1, further comprising at least one additional chelating agent.

17. The composition of claim 16, wherein the at least one additional chelating agent is selected from ethylene diaminetetraacetic acid (EDTA), sodium or potassium salts of EDTA, cyclodextrin, pentasodium pentetate, potassium citrate, potassium gluconate, sodium gluconate, and mixtures thereof.

18. The composition of claim 2, further comprising at least one chelating agent.

19. The composition of claim 18, wherein the at least one chelating agent is selected from ethylene diaminetetraacetic acid (EDTA), sodium or potassium salts of EDTA, cyclodextrin, pentasodium pentetate, phytic acid, potassium citrate, potassium gluconate, sodium gluconate, and mixtures thereof.

20. The composition of claim 3, further comprising at least one additional chelating agent.

21. The composition of claim 20, wherein the at least one additional chelating agent is selected from ethylene diaminetetraacetic acid (EDTA), sodium or potassium salts of EDTA, cyclodextrin, pentasodium pentetate, potassium citrate, potassium gluconate, sodium gluconate, and mixtures thereof.

22. A sunless tanning composition comprising at least one self-tanner selected from dihydroxyacetone or erythrulose, at least one vitamin D compound, ethoxydiglycol, glycerin, hydrolyzed soy protein, phenoxyethanol, glycolic acid, lactic acid, panthenol, *Phyllanthus emblica* fruit extract, disodium EDTA, phytic acid, *Salix alba* (willow) bark extract, phospholipids, ascorbyl palmitate, retinyl palmitate and tocopheryl acetate.

* * * * *